United States Patent
Aust et al.

(10) Patent No.: US 6,528,680 B1
(45) Date of Patent: Mar. 4, 2003

(54) METHOD FOR THE PRODUCTION OF PHOSPHONOMETHYLGLYCINE

(75) Inventors: Nicola Christiane Aust, Büren (DE); Thomas Butz, Mannheim (DE); Martin Fischer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/048,572

(22) PCT Filed: Aug. 10, 2000

(86) PCT No.: PCT/EP00/07808

§ 371 (c)(1),
(2), (4) Date: Feb. 4, 2002

(87) PCT Pub. No.: WO01/12639

PCT Pub. Date: Feb. 22, 2001

(30) Foreign Application Priority Data

Aug. 11, 1999 (DE) .......................... 199 37 958

(51) Int. Cl.⁷ ................................................. C07F 9/38
(52) U.S. Cl. ......................................................... 562/17
(58) Field of Search ............................... 562/8, 10, 16, 562/17

(56) References Cited

U.S. PATENT DOCUMENTS

| 4,369,142 A | * | 1/1983 | Moser | 562/17 |
| 4,486,358 A | * | 12/1984 | Moser | 562/17 |
| 4,952,723 A | * | 8/1990 | Fields et al. | 562/17 |
| 4,983,764 A | * | 1/1991 | Pelyva et al. | 562/17 |
| 5,023,369 A | | 6/1991 | Fields, Jr. | 562/17 |
| 5,043,475 A | * | 8/1991 | Fields, Jr. | 562/17 |
| 5,047,579 A | | 9/1991 | Glowka et al. | 562/17 |
| 5,077,431 A | * | 12/1991 | Fields, Jr. | 562/17 |
| 5,095,140 A | | 3/1992 | Fields, Jr. | 562/17 |

OTHER PUBLICATIONS

CA:121:157871 abs of BR 9300433 Sep. 9, 1993.*

CA: 133:105158 abstract of BR9601581 Jul. 27, 1999.

* cited by examiner

*Primary Examiner*—Jean F. Vollano
(74) *Attorney, Agent, or Firm*—Keil & Weinkauf

(57) ABSTRACT

The present invention relates to a process for the preparation of phosphonomethylglycine in which N-phosphonomethyliminodiacetic acid N-oxide is brought into contact with a catalytically active quantity of at least one catalyst, selected from amongst a thionyl halide, ammonium dithionite or an alkali metal dithionite, a dialkyl sulfite, sulfur dichloride, sulfur dioxide and sulfurous acid, in a reaction chamber by metering the N-phosphonomethyliminodiacetic acid N-oxide into the reaction chamber in such a way that always at least 50% of the N-oxide metered into the reaction chamber are converted.

14 Claims, No Drawings

METHOD FOR THE PRODUCTION OF PHOSPHONOMETHYLGLYCINE

This is a 371 PCT EPD 0/07808 filed Aug. 10, 2000 now WO 0/12639.

The present invention relates to a process for the preparation of phosphonomethylglycine from N-phosphonomethyliminodiacetic acid N-oxide.

Phosphonomethylglycine, which is known under the common name glyphosate, is a potent phytotoxic compound which is employed as herbicide.

EP-A-439445 describes the preparation of phosphonomethylglycine starting from N-phosphonomethyliminodiacetic acid. The latter is oxidized with a peroxide in aqueous solution, if appropriate in the presence of a catalytically acting quantity of a water-soluble molybdenum compound, to give the intermediate N-phosphonomethyliminodiacetic acid N-oxide. The N-oxide is subsequently converted into phosphonomethylglycine in the presence of a catalytic quantity of a metabisulfite compound and a water-soluble molybdenum compound.

EP-A-464017 also describes a process for the preparation of phosphonomethylglycine starting from phosphonomethyliminodiacetic acid using the same process steps. The oxidation to give the abovementioned N-oxide is carried out with a peroxide in the presence of a water-soluble molybdenum or tungsten compound. The conversion into phosphonomethylglycine is then carried out using iron, zinc, aluminum, vanadium or copper in the form of the metal or using a vanadium salt, iron(II) salt or copper(I) salt as catalyst.

Finally, EP-A-464018 also describes a process for the preparation of phosphonomethylglycine, the oxidation of the phosphonomethyliminodiacetic acid being carried out with a peroxide in the presence of a water-soluble tungsten compound or a mixture of a water-soluble tungsten and molybdenum compound as catalyst. The N-oxide is then brought into contact with iron metal, a water-soluble vanadium compound, an iron(II) salt or a mixture of a water-soluble sulfide, sulfite or bisulfite compound and a water-soluble molybdate compound and converted into phosphonomethylglycine.

The processes described in the prior art have in common that the catalyst is introduced into an initial charge of an aqueous solution of the N-oxide. On an industrial scale, the control of these methods requires great complexity since the gas which is formed upon conversion of the N-oxide into phosphonomethylglycine is liberated in an uncontrolled fashion and, moreover, the temperature of the reaction mixture climbs sharply.

It is an object of the present invention to provide a process for the preparation of phosphonomethylglycine which can be controlled, even on an industrial scale.

We have found that this object is achieved by a process for the preparation of phosphonomethylglycine in which N-phosphonomethyliminodiacetic acid N-oxide is brought into contact with a catalytically active quantity of at least one catalyst, selected from amongst a thionyl halide, ammonium dithionite or an alkali metal dithionite, a dialkyl sulfide, sulfur dichloride, sulfur dioxide and sulfurous acid, in a reaction chamber in the presence or absence of a cocatalyst by metering the N-oxide into the reaction chamber in such a way that always at least 50% of the N-oxide metered into the reaction chamber are converted.

N-Phosphonomethyliminodiacetic acid N-oxide is known and can be prepared by a plurality of processes. For example, it can be synthesized in accordance with U.S. Pat. No. 3,950,402 or U.S. Pat. No. 3,954,848 or in accordance with HU 187,347 using peroxides in the presence of compounds of silver, iron, tin, lead, manganese or molybdenum. However, the N-oxide is preferably prepared by one of the processes described in the European Patent Applications EP 439445 A, EP 464017 A or EP 464018 A, where N-phosphonomethyliminodiacetic acid is brought into contact with a peroxide such as hydrogen peroxide, performic acid, peracetic acid, perbenzoic acid, peroxytrifluoroacetic acid, benzoyl peroxide, benzenepersulfonic acid and the like. Hydrogen peroxide is preferably used, in particular in at least stoichiometric quantities based on N-phosphonomethyliminodiacetic acid. The hydrogen peroxide is generally employed in a concentration in the range of 10 to 70% by weight, in particular 30 to 70% by weight. The reaction temperature is generally in the range of approximately 0° C. to 80° C., in particular approximately 20° C. to approximately 70° C.

The oxidation of N-phosphonomethyliminodiacetic acid is particularly preferably carried out in the presence of a catalytic quantity of a water-soluble molybdenum compound or a water-soluble tungsten compound or a mixture of these. Suitable molybdenum compounds are known to the skilled worker, and it is only necessary for them to be soluble in the reaction medium. Useful molybdenum compounds are, for example, alkali metal molybdates such as sodium molybdate, ammonium molybdate or alkali metal or ammonium polymolybdates such as ammonium or sodium dimolybdate.

Suitable tungsten compounds are also known to the skilled worker, and all that is required is for them to be soluble in the reaction medium. Useful tungsten compounds are, for example, tungstic acid, 1,2-tungstatophosphate and barium tungstate. Ammonium tungstate and alkali metal tungstates such as sodium tungstate and potassium tungstate are preferred.

The catalyst quantity can vary within wide limits. In general, approximately 0.01 to approximately 5.0% by weight, preferably approximately 0.01 to approximately 3.0% by weight of catalyst are used, based on the weight of N-phosphonomethyliminodiacetic acid.

The peroxide is generally employed in at least stoichiometric quantities. It is preferred to use a small excess, in particular approximately 1.02 to 1.20 mole equivalents, especially preferably 1.05 to 1.15 mole equivalents, based on the quantity of phosphonomethyliminodiacetic acid.

The oxidation of the N-phosphonomethyliminodiacetic acid takes place in aqueous medium, the N-phosphonomethyliminodiacetic acid first being suspended but at least partially dissolving during the course of the oxidation. The N-phosphonomethyliminodiacetic acid is expediently employed in high concentration, for example in the form of an up to 60% by weight, in particular up to 50% by weight, aqueous suspension. The N-phosphonomethyliminodiacetic acid is preferably employed in such a quantity that a solution is present after the oxidation has ended. The transition from suspension to solution indicates that the oxidation reaction has essentially ended since the N-oxide is much better soluble in water than the N-phosphonomethyliminodiacetic acid.

The conversion of the N-oxide to the desired phosphonomethylglycine is preferably effected starting from an aqueous solution of the N-oxide. The catalyst is also preferably used in the form of an aqueous solution. Sulfur dioxide can be employed as a gas, either as such or diluted with an inert gas such as nitrogen. Catalysts which are preferably used are sulfur dioxide or sulfurous acid, thionyl chloride, a dialkyl sulfite, in particular a di-$C_1$–$C_4$-alkyl sulfite such as dimethyl sulfite, or an alkali metal dithionite, in particular sodium dithionite, or mixtures of these.

The conversion of the N-oxide into phosphonomethylglycine is preferably effected in the presence of a cocatalyst to increase the conversion rate. Suitable cocatalysts are, for example, water-soluble vanadium salts such as vanadyl sulfate or water-soluble iron(II) salts such as iron(II) sulfate or iron(II) chloride. However, it is preferable to use a water-soluble molybdenum compound such as ammonium molybdate or an alkali metal molybdate such as sodium molybdate or an ammonium polymolybdate or alkali metal polymolybdate such as ammonium dimolybdate or sodium dimolybdate as cocatalyst. It is particularly preferred to use the same cocatalyst for the oxidation of the N-phosphonomethyliminodiacetic acid and for the subsequent conversion of the N-oxide, in particular one of the abovementioned molybdenum compounds.

In general, at least 0.01% by weight of catalyst is used, based on the amount of N-oxide. As a rule, an amount of 10% by weight, preferably not more than 8% by weight of catalyst can be employed, based on the N-oxide. The amount is preferably in the range of 0.01% by weight to approximately 6.0% by weight, in particular in the range from 0.1% by weight to 5% by weight, based on the N-oxide. If the N-oxide solution still contains residual unconsumed peroxide compound, which amount can readily be determined by redox titration, and if a catalyst is used which can be oxidized by this residue, it is expedient to increase the amount of catalyst by the proportion to be consumed by the peroxide compound.

The amount of cocatalyst is generally in the range of approximately 0.01 to approximately 30 mol %, preferably approximately 0.05 to approximately 10 mol %, based on the N-oxide. It is preferred to use the same compound, in particular a water-soluble molybdenum compound, as catalyst for the preparation of the N-oxide and as cocatalyst for the conversion of the latter into phosphonomethylglycine. Then, after the oxidation, the catalyst is not removed from the reaction mixture, so that addition of further cocatalyst for the subsequent conversion reaction can be dispensed with.

The reaction temperature for converting the N-oxide into phosphonomethylglycine is generally in the range of 10° C. to 100° C., in particular 30° C. to 80° C., and preferably 35° C. to 70° C. For the conversion reaction, the N-oxide can be brought into contact with the catalyst in the customary manner.

The contacting of the N-oxide with the catalyst is performed in such a way that the N-oxide is metered into the reaction chamber, in particular in the form of an aqueous solution. "Metering" is to be understood for the purposes of the invention that the N-oxide is introduced into the reaction chamber gradually, i.e. controlled in terms of time, and is brought into contact in the reaction chamber with the catalyst, in particular in the form of an aqueous solution. This can be done for example by gradually running in the N-oxide solution or by adding it portionwise in small quantities. It is not necessary for all the N-oxide to be metered in. Some of it, for example up to 20% or up to 10%, can be placed into the reaction chamber at the outset.

It is possible to introduce some or all of the catalyst into the reaction chamber at the outset. If only some of the catalyst is introduced at the outset, the remainder may also be metered into the reaction chamber, either simultaneously with the N-oxide or staggered in time. As an alternative, all of the catalyst may be metered into the reaction chamber, again simultaneously with the N-oxide or staggered in time.

When carrying out the reaction, however, it must always be ensured that at least 50%, preferably at least 70%, especially preferably at least 90%, of the N-oxide metered into the reaction chamber are converted. The conversion rate can be determined readily from the amount of carbon dioxide which is liberated during the conversion. Accordingly, the N-oxide is metered in in such a way that at least 50%, preferably at least 70% and especially preferably at least 90% of the carbon dioxide quantity which is expected to be obtained during the conversion reaction and which corresponds to the N-oxide quantity which has already been added are liberated with only a slight delay, in general not more than 15 minutes, before more of the N-oxide solution is added. As a rule, this is achieved by ensuring that at least 0.01 mol % of catalyst based on the N-oxide which has been already been metered in is present in the reaction mixture. If the evolution of carbon dioxide in the course of the conversion reaction slows down or ceases, more catalyst can be added to the reaction mixture or, if some of the catalyst is metered in, the latter can be metered in more rapidly.

The cocatalyst can be brought into contact with the N-oxide in the same manner as the catalyst.

In the conversion reaction, the phosphonomethylglycine precipitates as a solid when a concentration of approximately 1.0% by weight in the reaction mixture is exceeded. The reaction is therefore expediently carried out in such a way that most of the phosphonomethylglycine is obtained as solid. As a rule, this is the case when the concentration is chosen such that a suspension with at least 10% by weight of suspended phosphonomethylglycine is obtained.

The phosphonomethylglycine can be separated from the suspension obtained by the customary techniques for isolating solids. Before the separation, the mixture is expediently cooled to <30° C., in particular to 10 to 20° C. and/or stirred for 1 to 20 hours. At least some of the mother liquor which remains after the phosphonomethylglycine has been separated, and which still contains dissolved phosphonomethylglycine and the catalyst, can be employed for the conversion of more N-oxide.

The preparation of the N-oxide and the subsequent conversion of the N-oxide into phosphonomethylglycine can be carried out as a batch, semi-batch (metering in hydrogen peroxide or N-oxide solution and, if desired, some of the catalyst) or continuously (all components, i.e. N-phosphonomethyliminodiacetic acid, oxidant and, if desired, catalyst or N-oxide, catalyst and, if desired, cocatalyst are metered in simultaneously).

The examples which follow illustrate the invention without imposing any limitation.

EXAMPLE 1

38 g of N-phosphonomethyliminodiacetic acid and 0.92 g of ammonium molybdate tetrahydrate are suspended in 100 ml of water and the suspension is warmed to 65° C. Then, 20.6 g of a 30% strength hydrogen peroxide solution are added dropwise in the course of 30 minutes, and stirring is continued for one hour at 65° C., during which process a clear solution forms. The test for $H_2O_2$ is negative. This N-oxide solution is added dropwise at 40° C. in the course of 30 minutes to 10 ml of an $SO_2$-saturated aqueous solution. A constant evolution of gas is observed. A colorless precipitate forms even while the N-oxide is being metered in. Then, stirring is continued for 1 hour at 40° C. The precipitate which has separated out is filtered and dried at room temperature. This procedure allows 23.2 g of N-phosphonomethylglycine with a purity of 96% to be isolated. This corresponds to a yield of 79% based on the amount of N-phosphonomethyliminodiacetic acid employed.

EXAMPLE 2

38 g of N-phosphonomethyliminodiacetic acid and 0.92 g of ammonium molybdate tetrahydrate are suspended in 100 ml of water and the suspension is warmed to 65° C. Then, 20.6 g of a 30% strength hydrogen peroxide solution are added dropwise in the course of 30 minutes, and stirring is continued for one hour at 65° C., during which process a clear solution forms. The test for $H_2O_2$ is negative. The solution is cooled to room temperature. The N-oxide solution is added dropwise in the course of 30 minutes to 10 ml of water through which a gas mixture of $SO_2$ and $N_2$ has been passed. During addition of the N-oxide, more mixture of $SO_2$ and $N_2$ is metered into the solution. A constant evolution of gas is observed and the temperature climbs to 55° C. The mixture is then stirred for 30 minutes at 5° C. The precipitate which has separated out is filtered off and dried. This procedure allows 22.0 g of N-phosphonomethylglycine with a purity of 98% to be isolated. This corresponds to a yield of 76% based on the amount of N-phosphonomethyliminodiacetic acid employed.

EXAMPLE 3

60 g of N-phosphonomethyliminodiacetic acid and 1.23 g of ammonium molybdate tetrahydrate are suspended in 75 ml of water and this suspension is warmed to 55° C., Then, 19.8 g of 50% strength hydrogen peroxide solution are added dropwise in the course of 15 minutes and stirring is continued for 1.5 hours at 65° C., during which process a clear solution forms. In the next step, 2 ml of saturated $SO_2$ solution and 15% of the N-oxide solution prepared are introduced into a reaction vessel at 40° C. N-Oxide is then added dropwise in such a way that the molar amount of $CO_2$ formed corresponds to approximately 70% of the molar amount of N-oxide which has been added dropwise. Thus, for example, after a total of 30% of the N-oxide solution has been run in, 1.7 l of $CO_2$ have formed. This procedure prevents the accumulation of N-oxide in the solution. If $CO_2$ evolves at a lower rate, the $SO_2$ solution is added in such a way that the amount of formed, in turn, corresponds to approximately 70% of the N-oxide which has been added dropwise. In this manner, $CO_2$ is evolved continuously. After all the N-oxide solution and 15 ml of $SO_2$ solution have been added dropwise in the course of 1.5 hours, no evolution of gas can be observed any longer after a further 15 minutes. In total, 4.3 l of $CO_2$ have formed. The solution is cooled to room temperature and the precipitate which has separated out is filtered off with suction and dried. 35 g of pure N-phosphonomethylglycine are isolated, which corresponds to a yield of 78% based on the amount of N-phosphonomethyliminodiacetic acid employed.

EXAMPLE 4

60 g of N-phosphonomethyliminodiacetic acid and 1.23 g of ammonium molybdate tetrahydrate are suspended in 75 ml of water and this suspension is warmed to 55° C. Then, 19.8 g of 50% strength hydrogen peroxide solution are added dropwise in the course of 15 minutes and stirring is continued for 1.5 hours at 65° C., during which process a clear solution forms. In the next step, 5 drops of thionyl chloride and 20 ml of the N-oxide solution prepared are introduced into a reaction vessel at 40° C., and N-oxide solution is added dropwise in 10 ml portions. If it emerges that gas is evolved at a lower rate when more N-oxide is added, the evolution of gas is kept constant by further dropwise addition of thionyl chloride. After all the N-oxide solution and 18 drops of thionyl chloride have been added dropwise in the course of 1.5 hours, no evolution of gas can be observed any longer after a further hour. In total, 4 l of $CO_2$ have formed. The solution is cooled to room temperature and the precipitate which has separated out is filtered off with suction and dried. 41.0 g of N-phosphonomethylglycine are isolated in a purity of 79%, which corresponds to a yield of 73% based on the amount of N-phosphonomethyliminodiacetic acid employed.

EXAMPLE 5

38 g of N-phosphonomethyliminodiacetic acid and 0.92 g of ammonium molybdate tetrahydrate are suspended in 100 ml of water and the suspension is warmed to 65° C. Then, 20.6 g of a 30% strength hydrogen peroxide solution are added dropwise in the course of 20 minutes, and stirring is continued for 40 minutes at 65° C., during which process a clear solution forms. The test for $H_2O_2$ is positive. 1.0 g of sodium dithionite dissolved in 15 ml of water are introduced into a reaction vessel. The N-oxide solution is metered in at 40° C. in the course of 75 minutes, during which time gas is constantly evolved. Stirring is then continued for 1.5 hours at 40° C. The precipitate which has separated out is filtered off and dried at room temperature. This procedure allows 19.2 g of pure N-phosphonomethylglycine to be isolated. This corresponds to a yield of 68% based on the amount of N-phosphonomethyliminodiacetic acid employed.

EXAMPLE 6

38 g of N-phosphonomethyliminodiacetic acid and 0.92 g of ammonium molybdate tetrahydrate are suspended in 100 ml of water and the suspension is warmed to 65° C. Then, 20.6 g of a 30% strength hydrogen peroxide solution are added dropwise in the course of 30 minutes, and stirring is continued for 1 h at 65° C., during which process a clear solution forms. The solution is cooled to 40° C., and 2.1 g of sulfur dichloride are subsequently metered in dropwise. Stirring is continued for 1.5 hours at 40° C. The precipitate which has separated out is filtered off and dried at room temperature. This procedure allows 21.0 g of N-phosphonomethylglycine with a purity of 95% to be isolated. This corresponds to a yield of 71% based on the amount of N-phosphonomethyliminodiacetic acid employed.

EXAMPLE 7

38 g of N-phosphonomethyliminodiacetic acid and 0.92 g of ammonium molybdate tetrahydrate are suspended in 100 ml of water and the suspension is warmed to 65° C. Then, 20.6 g of a 30% strength hydrogen peroxide solution are added dropwise in the course of 20 minutes, and stirring is continued for 40 minutes at 65° C., during which process a clear solution forms. 1.8 g of dimethyl sulfite dissolved in 15 ml of water are introduced into a reaction vessel. The N-oxide solution is metered in at 40° C. in the course of 75 minutes, during which time gas is constantly evolved. Stirring is then continued for 1.5 hours at 40° C. The precipitate which has separated out is filtered off and dried at room temperature. This procedure allows 21.5 g of pure N-phosphonomethylglycine to be isolated. This corresponds to a yield of 76% based on the amount of N-phosphonomethyliminodiacetic acid employed.

EXAMPLE 8

3550 l of water per hour are pumped into a 6 $m^3$ stirred vessel, and 2500 kg/h phosphonomethyliminodiacetic acid are metered in using a cellular-wheel sluice. The resulting suspension and, synchronously, a solution of 870 kg/h 50% strength hydrogen peroxide and 450 kg/h of a solution of 12% by weight ammonium molybdate in water are pumped into a 6 m$^3$ stirred vessel. The reaction vessel is cooled with water via a cooling jacket in such a way that a temperature of 65° C. is established with stirring.

The reaction mixture is pumped continuously into a second 6 m$^3$ vessel in which it is also stirred at 65° C. From there, it is pumped continuously into a third 6 m$^3$ stirred vessel into which a stream of 18,000 l/h sulfur dioxide is metered via a dip pipe. The temperature in the third reactor is set at 45° C. by means of the cooling jacket. The gas current of 220 m$^3$/h carbon dioxide which is evolved is absorbed in a scrubber operated with sodium hydroxide solution.

The suspension is pumped into a fourth 6 m$^3$ stirred vessel held at 50° C. Here, a further 27 m$^3$/h carbon dioxide are released, which are also fed to the scrubber.

The suspension of phosphonomethylglycine in water which this vessel contains is pumped into a 6 m$^3$ vessel, in which it is cooled to 20° C. From there, the suspension is fed continuously to a centrifuge in which 1767 kg/hh wet N-phosphonomethyglycine with a dry-matter content of 90% are separated from the aqueous filtrate.

We claim::

1. A process for the preparation of N-phosphonomethylglycine, wherein N-phosphonomethyliminodiacetic acid N-oxide is brought into contact with a catalytically active quantity of at least one catalyst, selected from amongst a thionyl halide, ammonium dithionite or an alkali metal dithionite, a dialkyl sulfite, sulfur dichloride, sulfur dioxide and sulfurous acid, in a reaction chamber by metering the N-phosphonomethyliminodiacetic acid N-oxide into the reaction chamber in such a way that always at least 50% of the N-oxide metered into the reaction chamber are converted.

2. A process as claimed in claim 1, wherein the catalyst used is sulfur dioxide, sulfurous acid, thionyl chloride, a dialkyl sulfite or an alkali metal dithionite.

3. A process as claimed in claim 1, wherein a cocatalyst is additionally employed.

4. A process as claimed in claim 3, wherein the cocatalyst employed is a water-soluble molybdenum compound.

5. A process as claimed in claim 1, wherein the N-oxide is metered into an aqueous solution of the catalyst.

6. A process as claimed in claim 1, wherein the N-oxide and the catalyst are metered into the reaction chamber simultaneously and separately.

7. A process as claimed in claim 1, wherein the N-phosphonomethyliminodiacetic acid N-oxide is metered in such a way that always at least 70% of the N-oxide metered into the reaction chamber are converted.

8. A process as claimed in claim 1, wherein the N-phosphonomethyliminodiacetic acid N-oxide is prepared by oxidizing N-phosphonomethyliminodiacetic acid.

9. A process as claimed in claim 8, wherein the oxidation is performed with a peroxide compound.

10. A process as claimed in claim 9, wherein the oxidation is performed in the presence of an oxidation catalyst.

11. A process as claimed in claim 10, wherein the same catalyst. is used as catalyst for oxidizing the N-phosphonomethyliminodiacetic acid and as cocatalyst for converting the N-oxide.

12. A process as claimed in claim 11, wherein N-phosphonomethyliminodiacetic acid is oxidized with a peroxide compound in the presence of a catalytically effective quantity of a water-soluble molybdenum compound to give N-phosphonomethyliminodiacetic acid N-oxide and the reaction mixture is subsequently brought into contact with the catalyst by metering it into the reaction chamber.

13. A process as claimed in claim 4 wherein the cocatalyst is ammonium molybdate or an alkali metal molybdate.

14. A process as claimed in claim 10 wherein the oxidation catalyst is a water-soluble molybdenum compound.

* * * * *